US008262641B2

(12) United States Patent
Vedrine et al.

(10) Patent No.: US 8,262,641 B2
(45) Date of Patent: Sep. 11, 2012

(54) FILLING SYSTEM AND METHOD FOR SYRINGES WITH SHORT NEEDLES

(75) Inventors: Lionel Vedrine, Ridgewood, NJ (US); Paul G. Alchas, Franklin Lakes, NJ (US); Christopher N. Cindrich, Draper, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 247 days.

(21) Appl. No.: 12/537,497

(22) Filed: Aug. 7, 2009

(65) Prior Publication Data
US 2009/0299325 A1 Dec. 3, 2009

Related U.S. Application Data

(62) Division of application No. 11/374,488, filed on Mar. 13, 2006, now abandoned.

(51) Int. Cl.
*A61M 5/32* (2006.01)
*A61B 19/00* (2006.01)
(52) U.S. Cl. ........................................ 604/411; 604/414
(58) Field of Classification Search .......... 604/403–416, 604/90, 117, 239, 240, 257
See application file for complete search history.

(56) References Cited

U.S. PATENT DOCUMENTS

| 527,958 | A |   | 10/1894 | Shober, Jr. et al. |
|---|---|---|---|---|
| 3,882,909 | A |   | 5/1975 | Ogle |
| 4,128,098 | A |   | 12/1978 | Bloom et al. |
| 4,215,151 | A |   | 7/1980 | Rios et al. |
| 4,576,211 | A |   | 3/1986 | Valentini et al. |
| 4,631,057 | A |   | 12/1986 | Mitchell |
| 4,662,878 | A |   | 5/1987 | Lindmayer |
| 4,886,499 | A |   | 12/1989 | Cirelli et al. |
| 4,944,736 | A |   | 7/1990 | Holtz |
| 4,973,310 | A |   | 11/1990 | Kosinski |
| 5,211,638 | A | * | 5/1993 | Dudar et al. .................. 604/539 |
| 5,279,576 | A |   | 1/1994 | Loo et al. |
| 5,279,582 | A |   | 1/1994 | Davison et al. |
| 5,279,583 | A |   | 1/1994 | Shober et al. |
| 5,328,483 | A |   | 7/1994 | Jacoby |
| 5,338,310 | A |   | 8/1994 | Lewandowski |
| 5,344,417 | A |   | 9/1994 | Wadsworth, Jr. |
| 5,356,406 | A |   | 10/1994 | Schraga |

(Continued)

FOREIGN PATENT DOCUMENTS

EP 0311787 4/1989

(Continued)

*Primary Examiner* — Philip R Wiest
(74) *Attorney, Agent, or Firm* — Robert E. West

(57) ABSTRACT

A filling system for syringes utilizing short needles to be filled from a vial having a thick septum is described. The system may be useful in any situation where the septum or vial stopper of a medication container is thicker than the usable length of the needle on the delivery device. Preferably, the syringe is filled just prior to use. The short needle includes an optional limiter which only permits a certain predetermined length of the needle cannula to protrude beyond the limiter a distance which limits penetration of the needle tip into both the skin and a vial stopper. The system and adapter may be useful for needles having a protrusion distance from approximately 0.5 mm to 3 mm, or any needle with a protrusion length shorter that the thickness of a septum to be accessed. Furthermore, a device is provided with shielding capabilities to shield the needle of the device.

9 Claims, 15 Drawing Sheets

U.S. PATENT DOCUMENTS

| | | | |
|---|---|---|---|
| 5,360,408 A | 11/1994 | Vaillancourt | |
| 5,385,555 A | 1/1995 | Hausser | |
| 5,526,306 A | 6/1996 | Hikawa et al. | |
| 5,527,288 A | 6/1996 | Gross et al. | |
| 5,527,306 A | 6/1996 | Haining | |
| 5,772,652 A | 6/1998 | Zielinski | |
| 5,891,129 A | 4/1999 | Daubert et al. | |
| 5,893,397 A | 4/1999 | Peterson et al. | |
| 5,925,029 A | 7/1999 | Jansen et al. | |
| 6,063,068 A * | 5/2000 | Fowles et al. | 604/414 |
| 6,070,623 A | 6/2000 | Aneas | |
| 6,120,490 A | 9/2000 | Neftel | |
| 6,139,534 A | 10/2000 | Niedospial, Jr. et al. | |
| 6,258,078 B1 | 7/2001 | Thilly | |
| 6,358,236 B1 | 3/2002 | DeFoggi et al. | |
| 6,379,340 B1 | 4/2002 | Zinger et al. | |
| 6,478,788 B1 | 11/2002 | Aneas | |
| 6,494,865 B1 | 12/2002 | Alchas | |
| 6,537,263 B1 | 3/2003 | Aneas | |
| 6,569,123 B2 | 5/2003 | Alchas et al. | |
| 6,569,143 B2 | 5/2003 | Alchas et al. | |
| 6,601,721 B2 | 8/2003 | Jansen et al. | |
| 6,656,433 B2 | 12/2003 | Sasso | |
| 6,689,118 B2 | 2/2004 | Alchas et al. | |
| 6,706,031 B2 | 3/2004 | Manera | |
| 6,715,520 B2 | 4/2004 | Andreasson et al. | |
| D495,416 S | 8/2004 | Dimeo et al. | |
| 6,776,776 B2 | 8/2004 | Alchas et al. | |
| 6,843,781 B2 | 1/2005 | Alchas et al. | |
| 6,875,205 B2 | 4/2005 | Leinsing | |
| 7,140,401 B2 | 11/2006 | Wilcox et al. | |
| 2002/0045858 A1* | 4/2002 | Alchas et al. | 604/117 |
| 2009/0215151 A1 | 8/2009 | Brunham et al. | |

FOREIGN PATENT DOCUMENTS

| | | |
|---|---|---|
| WO | WO97/02853 | 1/1997 |
| WO | WO03/011378 | 2/2003 |
| WO | WO2005/105014 A1 | 11/2005 |

* cited by examiner

FILLING SYSTEM AND METHOD FOR SYRINGES WITH SHORT NEEDLES

CROSS REFERENCE TO RELATED APPLICATIONS

This application is a divisional of U.S. Ser. No. 11/374,488 filed Mar. 13, 2006 which claims the benefit of Provisional application 60/661,367 filed Mar. 14, 2005.

FIELD OF THE INVENTION

The present invention relates generally to filling of delivery devices for delivering substances such as drugs, vaccines and the like, and more specifically relates to a drug delivery system and device having a needle which has a relatively short protrusion length. More specifically, the present invention relates to a method and apparatus for filling an intradermal delivery device using a needle sized for intradermal delivery to fill the syringe.

BACKGROUND OF THE INVENTION

Intradermal injections are used for delivering a variety of substances. Many of these substances have proven to be more effectively absorbed into or react with the immune response system of the body when injected intradermally. Recently, clinical trials have shown that hepatitis B vaccines administered intradermally are more immunogenic if administered intramuscularly. In addition, substances have been injected intradermally for diagnostic testing, such as, for example using what is known in the art as the "Mantoux test" to determine the immunity status of the animal against tuberculosis and the immediate hypersensitivity status of Type I allergic diseases.

An intradermal injection is made by delivering the substance into the epidermis and upper layers of the dermis. Below the dermis layer is subcutaneous tissue (also sometimes referred to as the hypodermis layer) and muscle tissue, in that order. There is considerable variation in the skin thickness both between individuals and within the same individual at different sites of the body. Generally, the outer skin layer, epidermis, has a thickness between 50-200 microns, and the dermis, the inner and thicker layer of the skin, has a thickness between 1.5-3.5 mm. Therefore, a needle cannula that penetrates the skin deeper than about 3.0 mm has a potential of passing through the dermis layer of the skin and making the injection into the subcutaneous region, which may result in an insufficient immune response, especially where the substance to be delivered intradermally has not been indicated for subcutaneous injection.

The standard procedure for making an intradermal injection via the Mantoux technique is known to be difficult to perform, and therefore dependent upon experience and technique of the healthcare worker. This procedure is recommended to be performed by accessing the vial with the needle and aspirating the medication into the syringe, stretching the skin, orienting the bevel of short bevel needle cannula (in one embodiment, a 26G×½") upwardly and inserting the needle cannula to deliver a volume of 0.5 ml or less of the substance into the skin of an animal with the needle cannula being inserted into the skin at an angle varying from around 10-15 degrees relative to the plane of the skin to form a blister or wheal in which the substance is deposited or otherwise contained. Accordingly, the technique utilized to perform the standard intradermal injection is difficult and requires the attention of a trained nurse or medical doctor; however this method does have the advantage of allowing the filling of the syringe directly from the vial. FIG. 2 of US Published Application No. 2005-0203459 A1 to Alchas shows a conventional syringe being filled from a multi-dose vial, which demonstrates that the length of the needle must be sufficient to fully penetrate the septum of a vial in order to aspirate the medication. Inserting the needle to a depth greater than about 3.0 mm may results in a failed intradermal injection, as the substance being expelled through the cannula will be injected into the subcutaneous tissue of the animal. Further, the standard method is not suitable for self-administration of intradermal injections. However, this method does have the advantage of being able to use the same needle for penetrating the vial and filling as is used for performing the injection, allowing the practitioner to select a fixed needle, which reduces dead space.

For many drug substances, it may be desirable to fill the delivery device at the point of, and immediately prior to use. In this situation, the delivery device is normally filled from a multi-dose vial. A multi-dose vial may be more economical and it enables the user to fill the delivery device with the specific dose required. The multi-dose vial may be pre-filled with a liquid substance or with a dry substance. For example, it is now conventional to reduce certain drugs to a dry or powdered form to increase the shelf life of drugs and reduce inventory space and pre-fill (or fill at time of use) a syringe with diluent for reconstitution of the dry drug. Multi-dose vials may be sealed with an elastomeric stopper or septum of thickness exceeding 3 mm. Additionally, some vial septums are coated with hard materials like PTFE (e.g. Teflon® PTFE) which could damage the filling needle upon penetration. A needle on the delivery device may be used to pierce the stopper or septum and draw the drug substance from the vial into the delivery device, typically a syringe. The drug substance may then be administered using the delivery device, which is discarded after use, and the unit-dose vial may be stored for further use. One problem with using a short needle which is suitable for intradermal injection is that the needle used for injection, when penetrated into certain vials is not long enough to access the medication within the vial.

Vial adapters to aid in penetration of vials have been proposed in the past. Various designs have been proposed in the past to align the vial to the syringe. One example of such a device is related in U.S. Pat. No. 5,356,406 to Shraga. The design of this adapter is such that it provides guidance of the needle to the vial. The vial adapter of '406 requires the use of a needle of sufficient length to penetrate the septum of the vial. Another such example of a vial adapter is related in U.S. Pat. No. 4,944,736 Holtz. The design of this adapter is such that it provides guidance of the needle to the vial. In addition, the vial adapter of '736 requires the use of a needle of sufficient length to penetrate the septum of the vial.

Further, with the advent of viral infections that are transferred through contact with bodily fluids, it is desirable to enclose or conceal a needle cannula subsequent to administering an injection. Preferably, a delivery device should include a mechanism that is capable of enclosing a needle cannula immediately subsequent to administering the injection. If a needle is left uncovered for even a short period of time after administering an injection, such as, for example, while trying to reattach a needle cap, a biohazard exists. Therefore, it may be desirable to provide an intradermal delivery device with a means for enclosing the needle cannula that is simply designed, easy to use, and readily available immediately after administering an injection.

The use of intradermal delivery systems is expected to increase. Use of a "standard" length needle to deliver a drug substance intradermally has its shortcomings, some of which are identified above. It is not possible to use a delivery device having a needle length suited for intradermal injection to aspirate a syringe with drug substance from a standard multi-use vial. Thus, there are shortcomings in the prior art that prevent filling an intradermal injection using a "short" length needle and a multi-use vial. As a result, there is a need to pre-fill an intradermal device, or to use a "long" detachable needle for filling the device and a "short" detachable needle for the drug administration, resulting in dead space losses. It would be advantageous to have a drug delivery device capable of accessing substances stored in multi-dose vials and delivering such substances into the intradermal region of the skin without encountering the shortcomings described above.

SUMMARY OF THE INVENTION AND ADVANTAGES

An intradermal injection device with a reservoir within which a drug substance may be held is able to be filled from a vial having a thick septum through the short needle by utilizing the device and method of one aspect of the invention. In accordance with one embodiment, the needle assembly of the device to be filled is specifically designed for making intradermal injections; however the devices and methods of the invention may be useful in any situation where the septum or vial stopper of a medication container is thicker than the usable length of the needle on the delivery device. The needle assembly, in accordance with one embodiment, includes a penetration limiter which permits a certain predetermined length of the needle cannula to protrude beyond the limiter a distance which limits penetration of the needle tip into the intradermal space of the patient's skin. In accordance with one embodiment, the needle tip extends beyond the skin engaging surface a distance ranging from approximately 0.5 mm to 3 mm. The needle assembly may be secured to the syringe via a hub portion, which may be integrally formed in the syringe body or the hub portion may be separate and detachably secured by a Luer fit or equivalent attachment method. As may be appreciated from FIG. 3, it is not possible, using a device having a stationary limiter at the short lengths required for intradermal injection, to fill a reservoir from a conventional vial having a septum of a thickness greater than the protrusion of the needle. The distance the needle protrudes from the limiter is too short to adequately penetrate the depth of the septum and access the substance contained in the vial. Aspects of the present invention allow for access to a substance contained in a conventional vial by an intradermal needle device or assembly. Alternatively, it may be desirable to pre-fill the syringe with a diluent and use the devices and methods having aspects of the invention for mixing of diluent and active ingredient. Thus, standard methods for preserving the therapeutic and/or diagnostic substances, such as maintaining them in liquid or powder form in conventional vials for future use, may be used with the system of the present invention. Furthermore, using the intradermal filling devices having aspects of the present invention, it is possible to use conventional, inexpensive delivery devices such as fixed needle plastic syringes, in conjunction with the intradermal devices, which reduces dead-space and are often not appropriate for use as fill at time of use devices.

Aspects of the present invention also support the vial such that it does not need to be supported by the free hand during the drawing of medicament. Additionally, aspects of the invention are directed to providing systems and devices for guidance and/or retention of the syringe to the vial adapter. These same systems may optionally form components of a safety needle shielding system.

Aspects of the present invention provide a fluid transfer system for use in transferring a medical substance from a medication container having a septum with a pre-determined thickness into a delivery device. The delivery device has a reservoir adapted for storing a medical substance and a needle cannula attached to the delivery device with a lumen in fluid communication to the reservoir. The needle has a forward tip extending away from the delivery device a pre-selected usable length, wherein the usable length is less than a thickness of a septum of the medication container. The system utilizes an adapter body which includes a container receiving portion with a septum access needle, and a longitudinal projection extending from the adapter body. The projection includes an adapter septum having a thickness less than the usable length of the needle cannula. When the container is inserted into the container receiving portion and the delivery device needle is penetrated through the adapter septum, fluid communication is established to the substance in the container such that it is allowed to be aspirated into the reservoir. Optionally, the system further comprises a shield which is slidably disposed upon the delivery device. The shield has at least a two positions, a first position exposing the forward tip of the needle cannula and a second position concealing the forward tip of the needle cannula. Optionally, the system further comprises a shield which includes at least one slot wherein the slot cooperates with a corresponding feature on the vial adapter protrusion. Optionally, the vial adapter protrusion includes at least one locking finger or tang received by the slot in the shield. Optionally, the locking features are disposed in a helical pattern. In an alternate embodiment of the shield, the shield is slidably disposed upon the delivery device having at least a first position and a second position, the first position concealing said forward tip of said needle cannula and the second position exposing said forward tip of said needle cannula. Optionally, in this embodiment, a locking clip is used which is slidably disposed between the shield and the delivery device. The clip itself has at least two positions. A first position of the clip allows proximal movement of the shield with respect to the delivery device. The second position of the clip prevents proximal movement of the shield with respect to the delivery device. Optionally, movement of the shield with respect to the delivery device engages the clip and moves the clip into a second position of the clip, thereby preventing proximal movement of the shield with respect to the delivery device.

Additionally, a method of intradermally injecting a substance is provided including the steps of providing a vial adapter for use with a vial having a septum with a pre-selected thickness, and providing an intradermal injection device having a predetermined usable length of needle, inserting the vial into the vial adapter, inserting the intradermal device into the vial adapter, filling the intradermal device, removing the intradermal device from the vial adapter, and pressing the intradermal device to the patient's skin such that the skin engaging surface of the limiter encounters the skin and prevents penetration of the needle cannula deeper than about 3 mm; and injecting the substance under conditions and for a time sufficient to deliver the substance into the dermis layer of the skin.

Other aspects of the invention include a delivery device having a reservoir within adapted for storing a medical substance. The device includes a needle cannula attached to the delivery device having a lumen in fluid communication to the reservoir and having a forward tip extending away from the delivery device a pre-selected usable length. The device also includes a shield which is slidably disposed upon the delivery device having at least a first position and a second position. The shield's first position conceals the forward tip of the needle cannula and the second position exposing the forward tip of the needle cannula. The device also includes a locking clip which is slidably disposed between the shield bore and the delivery device. The clip has at least a first position and a second position, the clip's first position allows proximal movement of the shield with respect to the delivery device and the clip's second position prevents proximal movement of the shield with respect to the delivery device. In use, a first proximal movement of the shield with respect to the delivery device into the shield's second position engages the locking clip and moves the locking clip into the second position of the locking clip, thereby preventing subsequent proximal movement of the shield with respect to the delivery device. Optionally, the shield includes at least one slot wherein the slot cooperates on a corresponding feature on a medication vial protrusion, wherein the cooperation allows removable attachment of the delivery device to the container.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

As used herein, the term "proximal" and derivatives thereof, shall mean the end of an item or direction closest to the caregiver during use of the subject invention. The term "distal" and derivatives thereof, shall mean the end of an item or direction towards a patient during use of the subject invention. As used herein, the term "septum" and derivatives thereof shall mean any breachable barrier that is intended for sealing a fluid conduit or container, including, by way of non-limiting example, vial stoppers, cartridge stoppers, films, elastomeric rubber stoppers, and septum valves. As used herein, the term "drug substance" and derivatives thereof, shall mean any substance that is intended for injection into a patient, including, by way of non-limiting example, drugs, vaccines, therapeutics, and the like. It will be obvious to a person of skill in the art, and from the disclosure provided herein, that the subject invention is not limited or otherwise defined by the type or class of substance administered using the inventive injection device.

Figure 1:
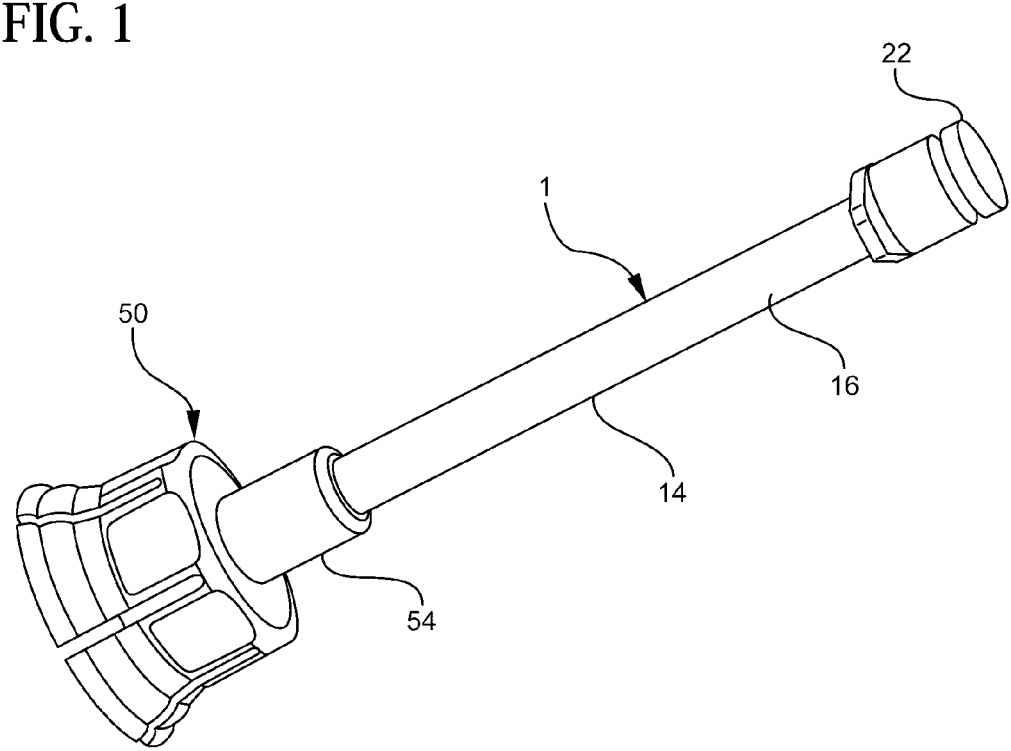
FIG. 1 shows an embodiment of an intradermal injection device having an intradermal needle assembly inserted into a vial adapter in accordance with one aspect of the invention, in perspective view.
Figure 2:
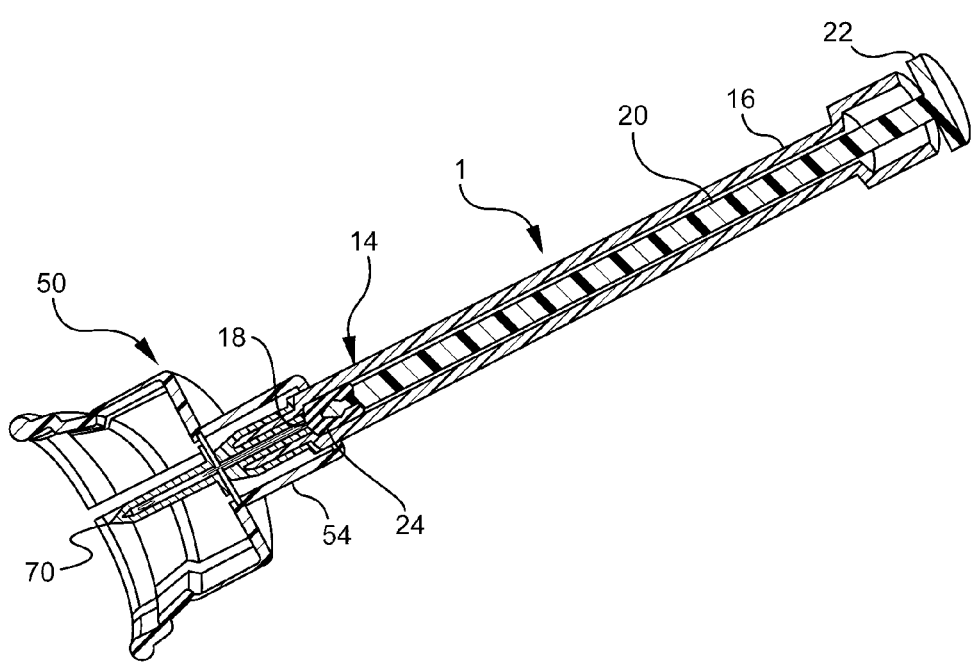
FIG. 2 shows a cross-sectional view of the assembly of FIG. 1.
Figure 3:
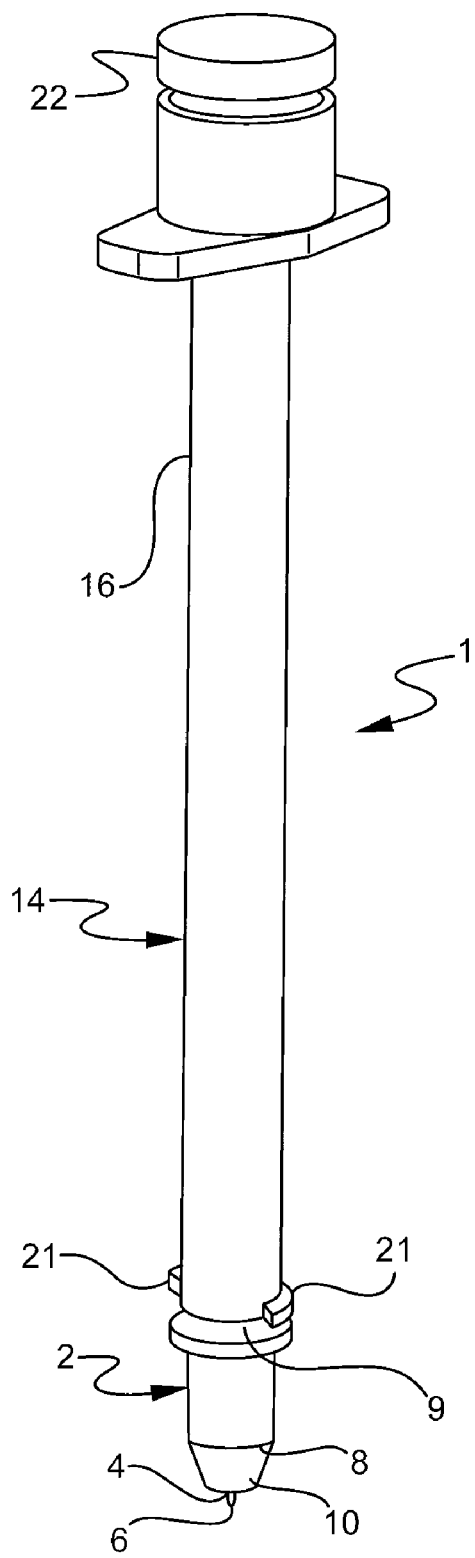
FIG. 3 shows a perspective view of an intradermal injection device as used in the assembly of FIG. 1.

FIGS. 1-3 shows an intradermal injection device 1 comprising a syringe 14 having a syringe body 16 that defines a reservoir 18 within which a drug substance may be held. A plunger 20 is disposed in the syringe body 16. Plunger 20 has a flange 22 at a distal end thereof and a stopper 24 at the opposed proximal end thereof. Device 1 has a needle assembly 2 secured to a distal end of the syringe body 16. An exemplary needle assembly 2 and intradermal injection device 1 of the type depicted in FIG. 3 is disclosed in U.S. Pat. Nos. 6,494,865; 6,569,143; 6,689,118; 6,843,781; 6,569,123; 6,776,776; and US Published Application No. 2005-0203459 A1 to Alchas and Alchas et al., the entire contents of each of which are incorporated by reference herein in their respective entireties. The needle assembly 2 is specifically designed for making intradermal injections. The needle assembly 2 carries a needle cannula 4 having a needle tip 6 at a distal end thereof. Alternatively, the needle cannula 4 may be secured directly to the syringe body 16. The needle assembly 2 may also includes a penetration limiter 8 having a hub portion 9 that may be secured to the syringe body 16, and a limiter portion 11 that defines a skin engaging surface 10 at a distal end of the limiter 8. The limiter 8, which generally surrounds the proximal end of the needle 4, permits a certain predetermined length of the needle cannula 4, including the needle tip 6, to protrude beyond the skin engaging surface 10 so that the distance between the needle tip 6 and skin engaging surface 10 limits penetration of the needle tip 6 into the intradermal space of the patient's skin. Preferably, the needle tip 6 of the needle cannula 4 extends beyond the skin engaging surface 10 a distance ranging from approximately 0.5 mm to 3 mm. The needle cannula 4 and skin engaging surface 10 are optionally arranged with respect to each other in a pre-determined angular relationship that serves to ensure a pre-determined angular relationship (e.g. generally perpendicular) between the needle cannula 4 and the patient's skin; such a pre-determined angular relationship being preferred when making intradermal injections. The skin engaging surface 10 engages the surface of the skin of a patient and would also limit the penetration depth of the needle tip 6 into a vial septum. The needle assembly 2 is secured to the syringe 14 via the hub portion 9, which may be fixedly secured to the syringe body 16, or the hub portion 9 may be secured by a Luer fit or equivalent attachment method. Alternatively, the needle assembly 2 may be integrally formed on the syringe body 16.

The substances for use with the device and method include vaccines and certain medicaments and drugs. Additionally, these substances can be used for diagnostic testing such as, for example, the Mantoux test to determine immunity status against tuberculosis and immediate hypersensivity status of Type I allergic diseases. Also, the substance intradermally delivered in accordance with aspects of the methods and devices of the present invention is selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atheroschlerosis malaria, E-coli, Alzheimers, H. Pylori, salmonella, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

In accordance with one embodiment of a medication container, these substances are stored in medication vials with an open end, a rim surrounding the open end and a reduced diameter neck portion adjacent the rim. The vial is sealed, in some embodiments with an elastomeric septum, which includes a portion inserted into the neck of the vial and a planar rim portion which overlies the vial rim. The septum is normally secured to the vial rim with an aluminum collar. In the case of a conventional syringe, the needle can be used to directly access a drug substance contained within the vial. In one embodiment, the minimum thickness of a standard vial septum is greater than 2 mm, nominally 3 mm and some are greater than 5 mm. Furthermore, at the edges of a vial stopper the thicknesses may exceed 8 mm. As described above, vial stoppers may also be coated with PTFE or other barrier coatings which not only add to the thickness, but add to the penetration resistance.

Figure 4:
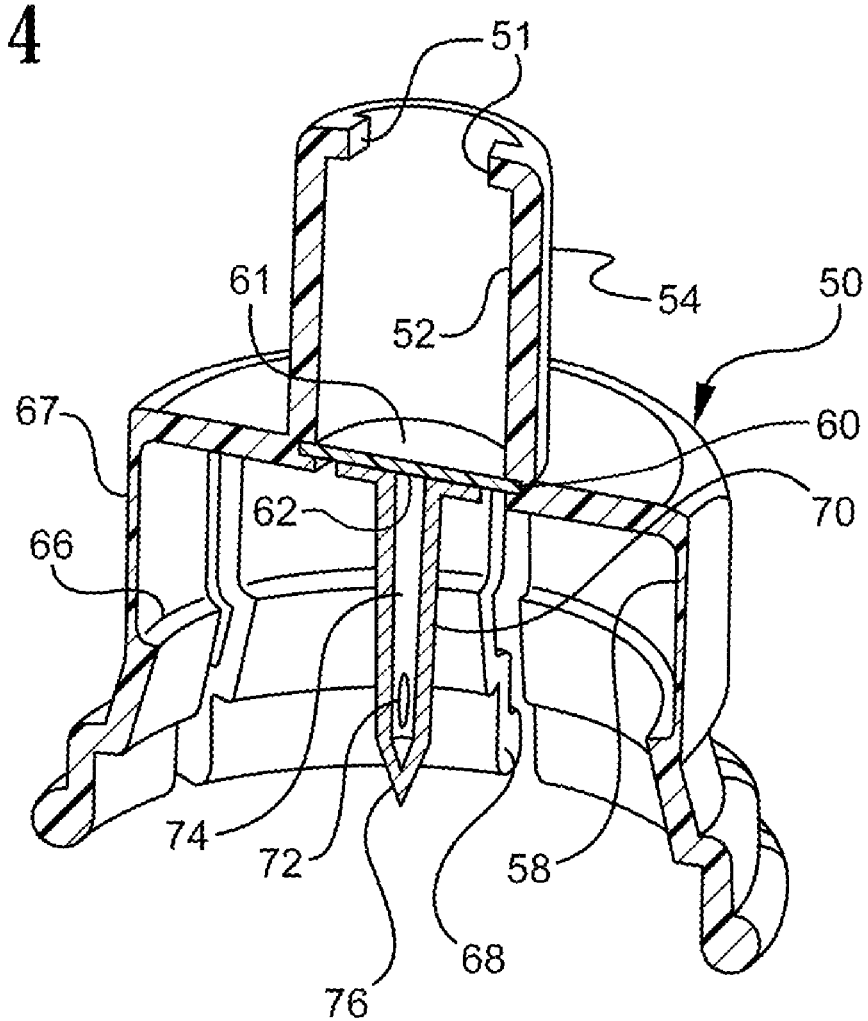
FIG. 4 shows a perspective cross-sectional view of the vial adapter of the assembly of FIG. 1.

When the needle 4 of intradermal injection device 1 not is sufficiently long to penetrate the septum to access the drug substance contained in the vial, the use of a vial adapter 50 may be employed in order to use needle 4 to fill the delivery device. Now referring to FIG. 4, vial adapter 50 includes protrusion 54 having a passage 52 adapted to receive at least a portion of needle assembly 2. At the proximal end of passage 52 is disposed septum 60. Septum 60 has a proximal face 61 and a distal face 62. At the distal end of vial adapter 50 is opening 58, adapted to receive a portion of the medication vial. Preferably, opening 58 is adapted to receive the aluminum collar of the medication vial. Disposed in opening 58 is vial spike 70 having a point 76 which is adapted to pierce the septum of the medication vial. Vial spike 70 is a generally hollow structure formed by lumen 74 and further includes aperture 72 disposed at the distal end of vial spike 70. The proximal end of vial spike 70 is fluid communication with distal face 62 of septum 60.

When the medication vial is inserted into opening 58, the distal end of vial spike 70 including aperture 72 is penetrated through the septum of the medication vial. Vial Spike 70 protrudes a predetermined distance preferably being in excess of about 5 mm from a portion of vial adapter 50 such that aperture 72 is able to enter the interior of the medication vial. Preferably, the protrusion of vial spike is in the range of about 8 mm to about 15 mm, more preferably, is in the range of about 10 mm to about 13 mm. The lumen 74 of vial spike 70 is in fluid communication with distal face 62 of septum 60. Furthermore, when the delivery device 1 is inserted into passage 52, the needle tip 6 and lumen of needle 4 of needle assembly 2 is able to pass the distal face 62 of septum 60 by the complete penetration of septum 60. Preferably, the tip 6 and a portion of the lumen of needle 4 are now within a portion of lumen 74 of vial spike 70, thus allowing fluid communication. The thickness of septum 60 is pre-selected such that the thickness of septum 60 is always less than the protrusion of needle 4 from limiter portion 11. Preferably, the thickness of septum 60 is in the range of about 0.01 mm to about 3 mm, more preferably, is in the range of about 0.25 mm to about 1 mm, more preferably, is in the range of about 0.5 mm to about 1 mm. In this embodiment the septum may be silicone or a suitable elastomer. Additionally, the septum may be pre-slit for easier penetration. In an alternate embodiment, the septum is a film having a thickness of between about ½ and about 4 mil. In a particular embodiment of film, the film is a thermoform able polyethylene terephthalate (PET). In a particular embodiment of film, the film is a co-laminated or co-extruded film including a layer of thermoform able polyethylene terephthalate (PET) on the exterior thereof and an optional layer of heat-sealable polyethylene on the interior thereof. In some of the embodiments, the septum 60 is heat sealed onto the vial adapter 50. In other embodiments septum 60 is retained mechanically within vial adapter 50. Thus, when vial adapter 50 is used to access a medication vial, fluid communication between the interior of the medication vial and the reservoir 18 is established through vial spike 70 and needle 4.

Opening 58 in vial adapter 50 may further include features to engage the vial while the vial is in opening 58. In one embodiment, vial adapter 50 is slit with a plurality of slits 68 which form a plurality of cantilevers 67. Cantilever 67 optionally includes lip 69 to help guide the medication vial into opening 58. When the medication vial is inserted into opening 58, cantilevers 67 are deflectable radially outward to allow medication vial to enter opening 58 with an interference fit. Cantilevers 67 optionally include shoulder 66 so that a portion of the medication vial is positively (and releasably) locked into opening 58. In an alternate embodiment, medication vial is permanently locked into opening 58 by selection of cantilever 67 and shoulder 66 dimensions which prevent the removal of the medication vial from opening 58.

In a preferred embodiment of the present invention, all components of the intradermal device 2 and the vial adapter are made from moldable plastic materials such as, for example, polymeric plastics such as polyethylene, polypropylene, polycarbonate, and the like (except for the needle cannula 4 which is preferably made from steel, and the septum 60 which is preferably made from materials as described above or an elastomeric material). This construction allows for the vial adapter 50 and vial spike 70 to be unitarily formed from a single moldable plastic. In an alternate embodiment, vial spike 70 is also constructed of steel. Furthermore, it may be possible to unitarily form septum 60 and vial adapter 50. These part reductions are especially helpful in ease of assembly as well as reducing costs of manufacture.

The vial adapter 50 may be supplied as an add-on to conventional drug delivery devices, i.e., glass or plastic syringes. In that case, the vial adapter 50 may be attached to a conventional medication vial and intradermal drug delivery device, such as a syringe at the point of use. Alternatively, the vial adapter 50 may be provided with an intradermal injection device 1, thus comprising a system in accordance with certain embodiments of the present invention. Generally, the vial adapter 50 and intradermal device 1 will be provided with a protective packaging to maintain the integrity of the unit and/or sterility thereof. The vial adapter 50 may further be provided with a protective cap to cover opening 58 and/or passage 52 prior to use thereof.

Now referring to FIGS. 6-9 which show an alternate embodiment having aspects of the present invention. In this particular embodiment, needle assembly 2 is detachable from syringe body 16. The attachment of syringe 14 to needle assembly 2 is by fitting 28. Fitting 28 provides for fluid commutation between needle 4 and reservoir 18. Preferably, fitting 28 is a luer taper; however, in certain applications it may be desirable to configure fitting 28 with a proprietary-type connection with syringe 14. Disposed on needle assembly 2 is tang catch 21 which engages tang 51 on adapter 50. Tang catch 21 and tang 51 may be utilized on any embodiment disclosed herein. Optionally, tang 51 is formed with a helical surface such that engagement of tang 51 and tang catch 51 so that relative rotational movement about a longitudinal axis induces linear movement of the two components (adapter 50 and needle assembly 2). This may be useful in applying additional forces which may be required to penetrate septum 60 with needle 4. Tang 51 and tang catch 21 may be optionally be formed with a bayonet-type fit such that a partial relative rotation about a longitudinal axis of the two components (adapter 50 and needle assembly 2) allows the two components to be removably attached.

Figure 5:
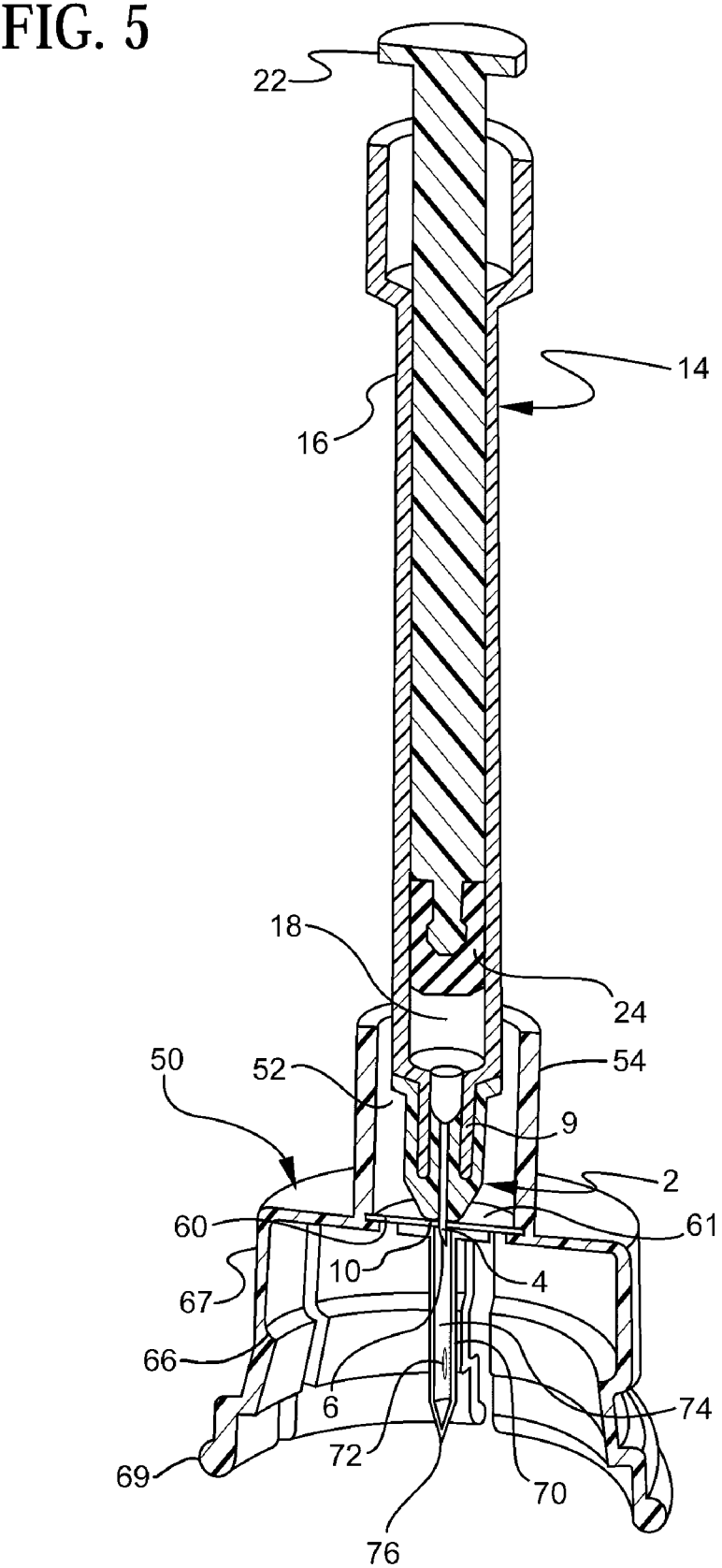
FIG. 5 shows a perspective cross-sectional view of the assembly of FIG. 1, with the plunger in a position to aspirate the medication.
Figure 6:
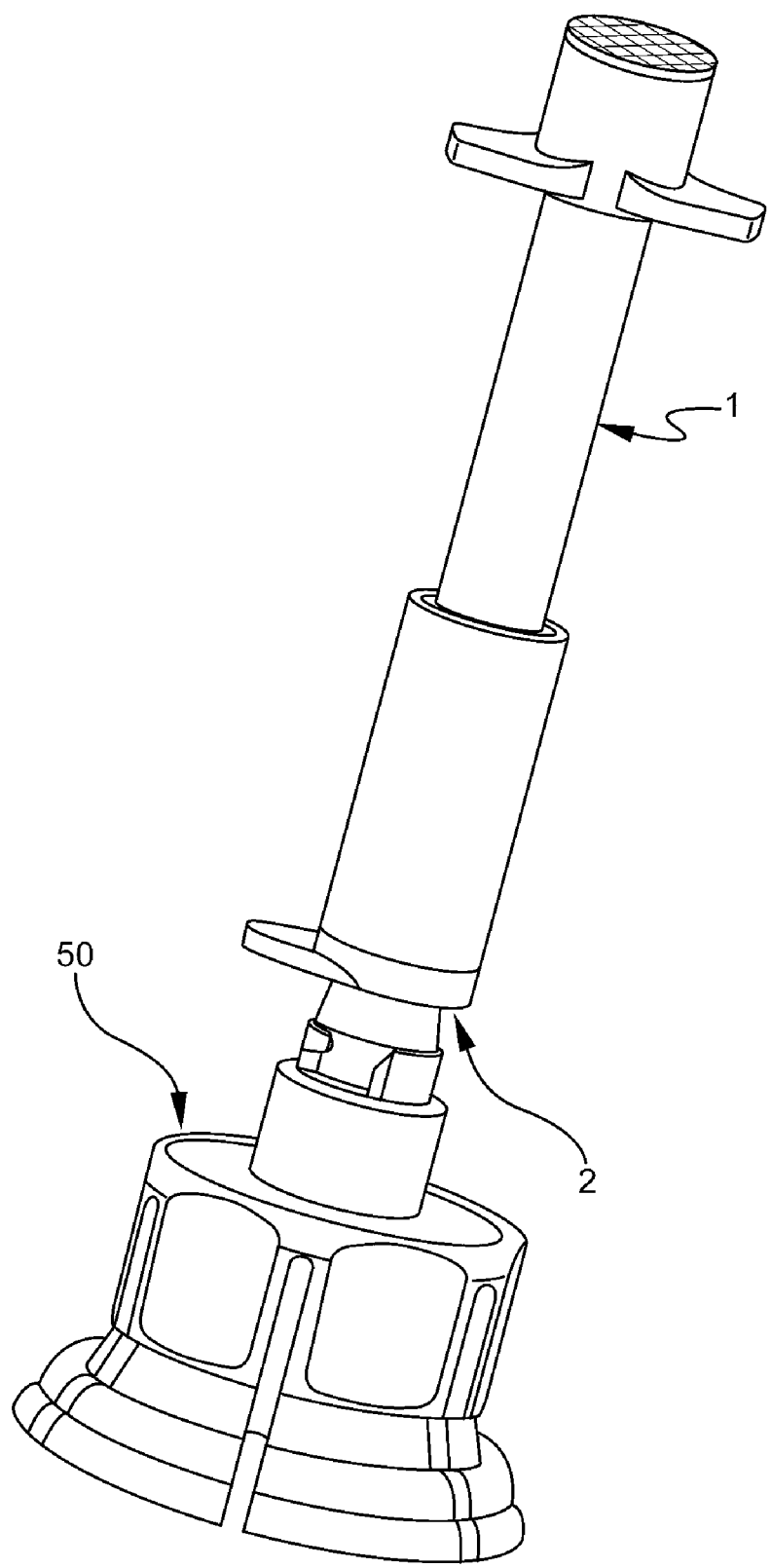
FIG. 6 shows a perspective view of an embodiment of an intradermal injection device having a detachable intradermal needle assembly inserted into a vial adapter in accordance with one aspect of the invention, in perspective view.
Figure 7:
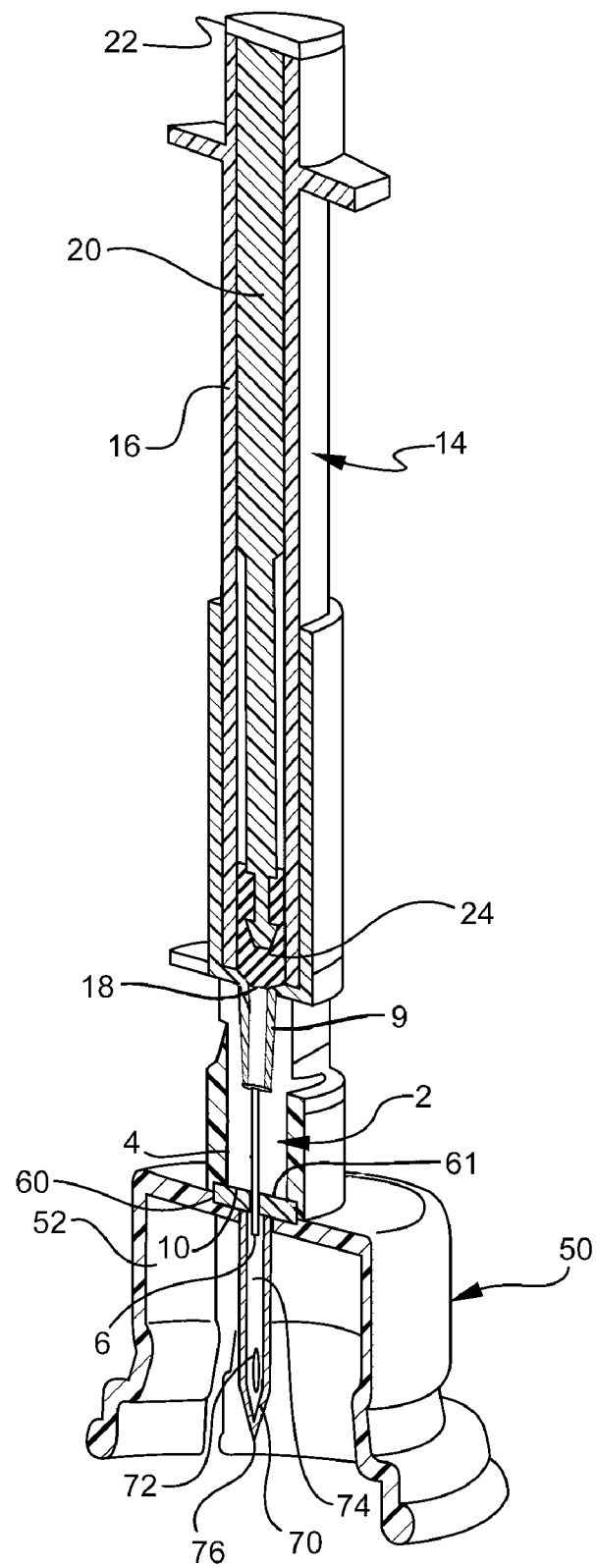
FIG. 7 shows a cross-sectional view of the assembly of FIG. 6.
Figure 8:
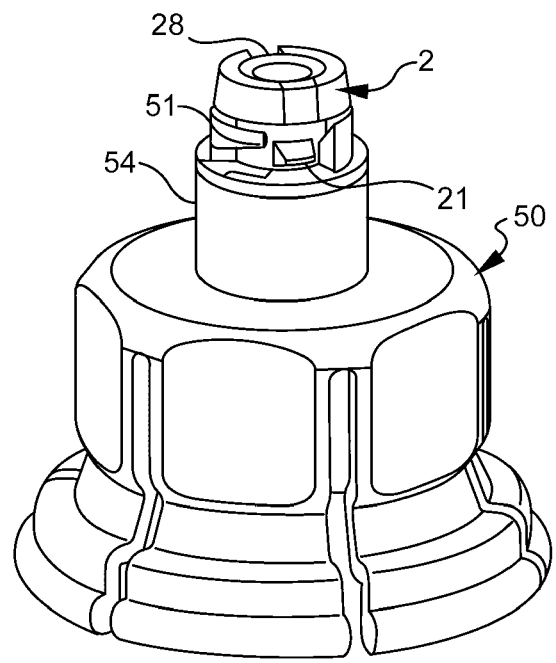
FIG. 8 shows a perspective view of the vial adapter of the assembly of FIG. 6 with the intradermal needle assembly attached.
Figure 9:
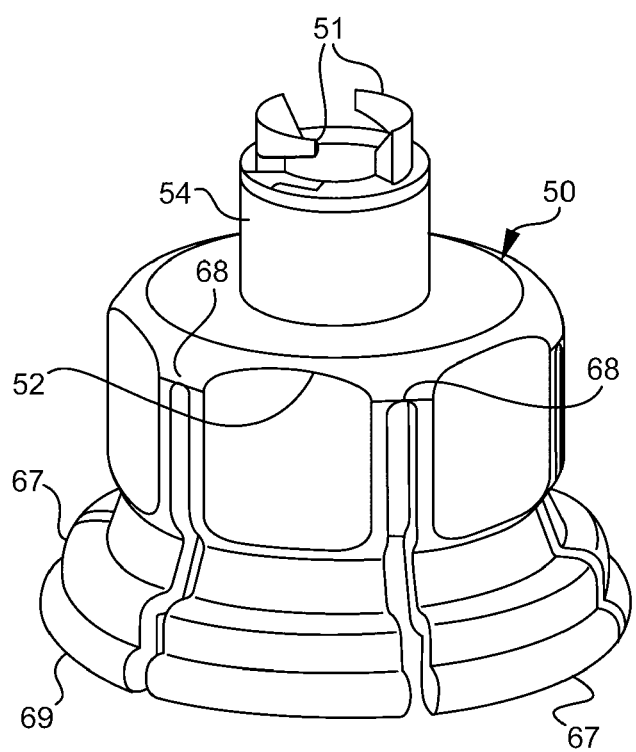
FIG. 9 shows a perspective view of the vial adapter of the assembly of FIG. 6.
Figure 10:
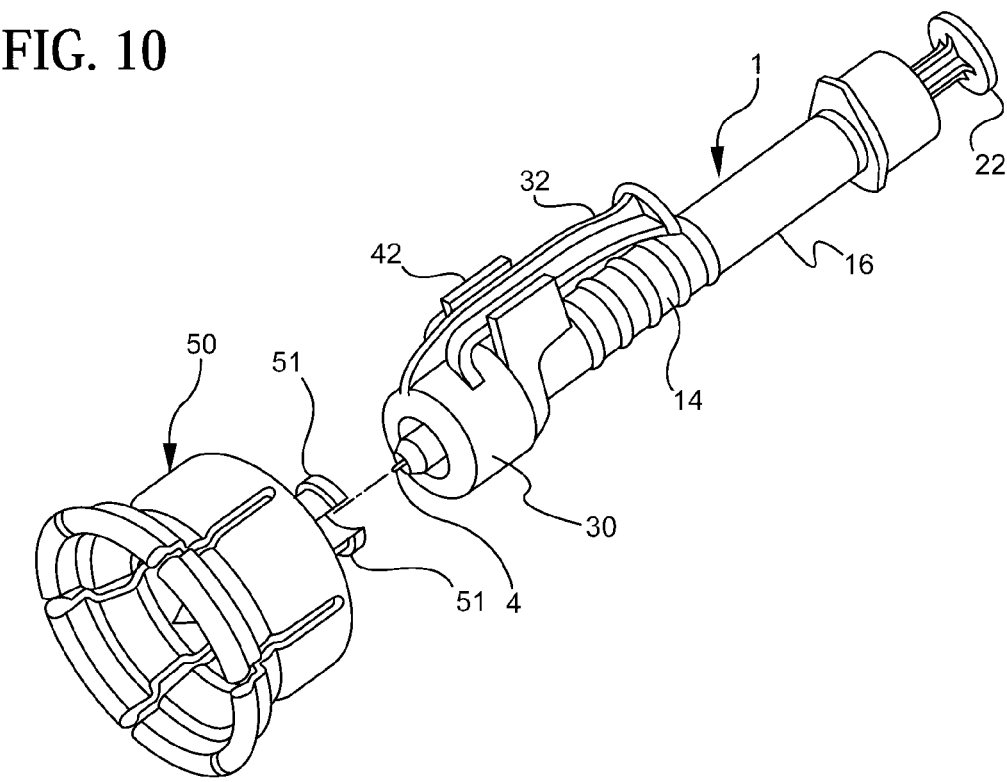
FIG. 10 shows an embodiment of an intradermal injection device having a shieldable intradermal needle assembly prior to insertion into a vial adapter in accordance with one aspect of the invention, in perspective view.

In use, a health care professional administering the intradermal injection will unwrap the protective packaging from the vial adapter 50 (if provided as a separate component) or injection device 1. If necessary, the injection device 1 can be filled with a diluent at this time, using methods that are conventional and known in the art. The health care professional will then manually insert the medication device into the vial adapter 50 in preparation for aspiration of medication into reservoir 18. If supplied as separate components, the health care professional will then manually insert the intradermal delivery device 1 into the vial adapter 50 (see, e.g., FIG. 5) in preparation for aspiration of medication. Alternatively, vial adapter 50 and delivery device 1 are pre-assembled. Optionally, at this point, a diluent is injected in the medication vial. The healthcare professional then aspirates the syringe with the medication from the medication vial from reservoir 18. The health care professional will then manually remove the medication device 1 from vial adapter 50 in preparation for administration of the intradermal injection. Administration will, in one embodiment, involve pressing the skin engaging surface 10 of the limiter 11 substantially perpendicular to a surface of the patient's skin. The drug substance will then be injected using the plunger 20 or other device conventionally used to deliver a drug substance. The injection will continue for a period of time determined by one having skill in the art based on the particular substance being administered as well as the dosage volume. Upon completion of the injection, the health care professional withdraws the needle cannula 4 from the patient's skin and disposes the used injection device 1 in a suitable container. Prior to disposal, the health care professional optionally activates the shielding portion of delivery device 1. A particular embodiment of shielding device is disclosed further below.

As will now be understood, the intradermal delivery device having aspects of the invention may include a needle enclosure means which encloses or conceals the needle cannula tip following injection and which preferably cannot be retracted to prevent accidental needle contact or reuse. In one embodiment shown in FIGS. 10-15, a shield may be extended following injection and locked in place. In a second embodiment shown in FIGS. 16-20, the assembly includes a re-extendable shield, which locks in the extended position, preventing contact with the needle by use of shield clip for example, as is disclosed in U.S. Pat. Nos. 5,338,310; 5,385,555 and 4,631, 057 each of the disclosure of which are incorporated by reference herein in their entirety. Alternatively, the assembly may include a plunger lock via a plunger clip as disclosed, for example, in a copending US Publication 2005/0027250A1 or U.S. Pat. Nos. 4,973,310 and 4,961,728 the disclosure of which is incorporated by reference. The plunger lock may also configured to lock the shield as is described below. The syringe barrel has an elongate body portion, a proximal end, and a distal end, and a needle at the distal end. A metal locking element is positioned in the shield between the barrel and the inside surface of the shield. The outside surface of the syringe barrel acts as a pathway for the longitudinal motion of the locking element relative to the elongate body portion. The element includes a proximal portion and a distal portion, an optional proximally and outwardly facing locking barb, a distally and inwardly facing resisting edge and an inwardly facing driving edge at the proximal portion of the element. The driving edge is adapted to interact with the outer portion of the syringe barrel to move the locking element along the bore of the shield as the barrel is advanced proximally along the barrel by force applied to the shield. The resisting edge and the barb are adapted to prevent motion of the barrel with respect to the shield after initial proximal motion of the shield.

Now referring to FIG. 10-13, which show an alternate embodiment having aspects of the present invention. In this particular embodiment, needle assembly 2 is integral to syringe body 16 and includes threads 25 which engages tang 51 on adapter 50. Threads 25 and tang 51 may be utilized on any embodiment disclosed herein. In this embodiment, threads 25 are formed with a helical surface such that engagement of tang 51 and threads 25 is helical in nature and allows for positive connection of the two components (Device 1 and adapter 50).

Figure 13:
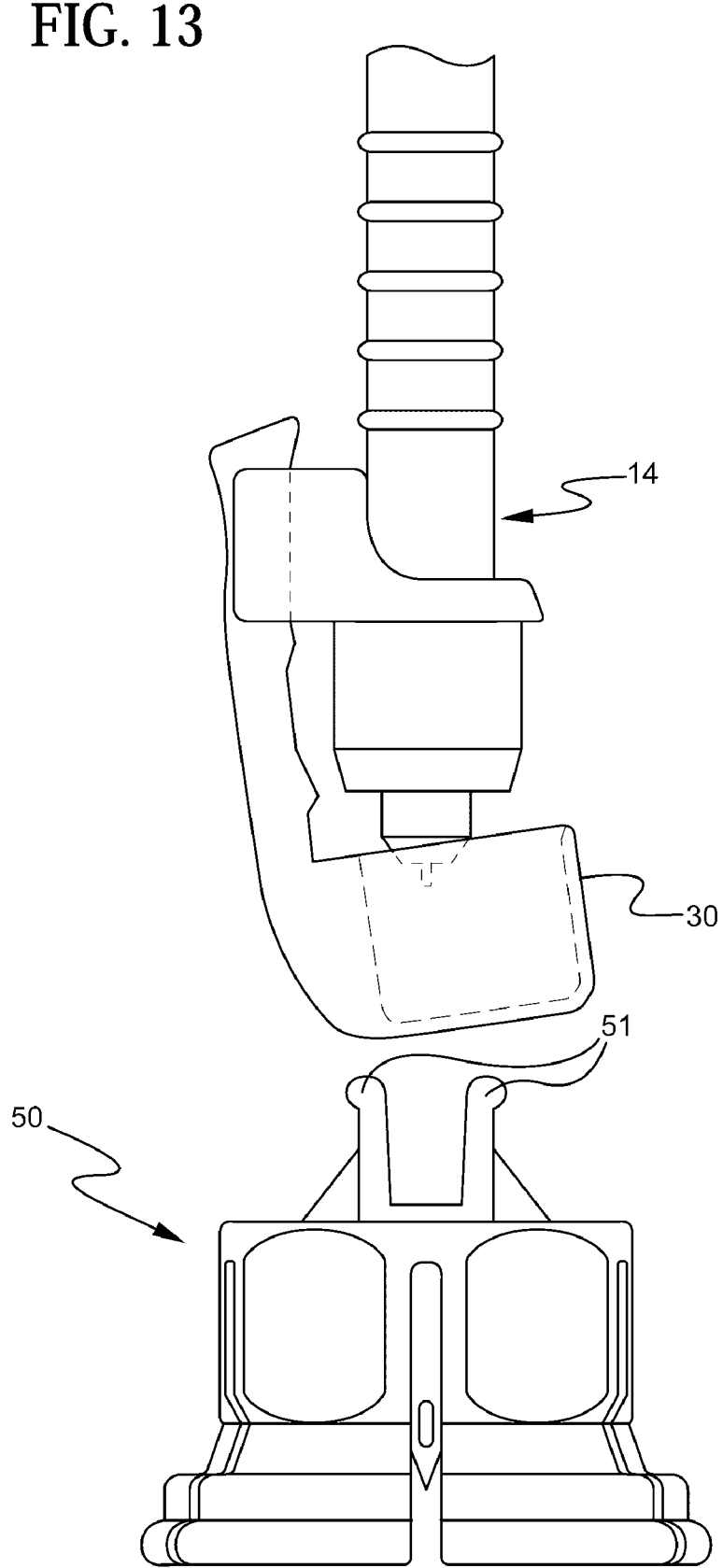
FIG. 13 shows a side view of the assembly of FIG. 10 with the shield activated.
Figure 14:
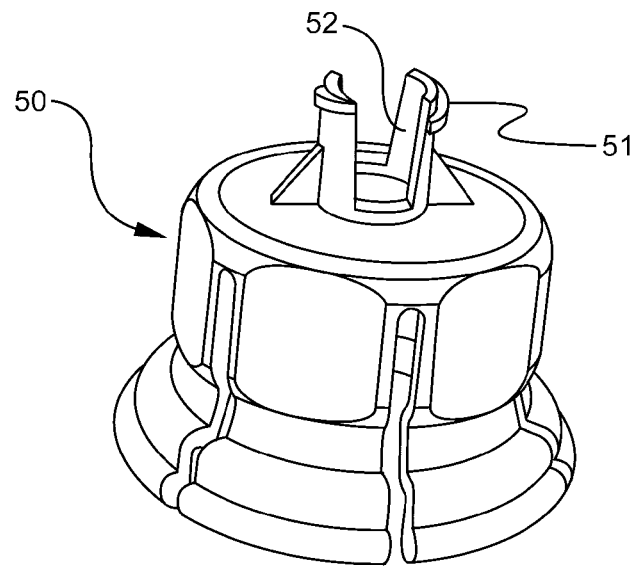
FIG. 14 shows a perspective view of the vial adapter of the assembly of FIG. 10.
Figure 15:
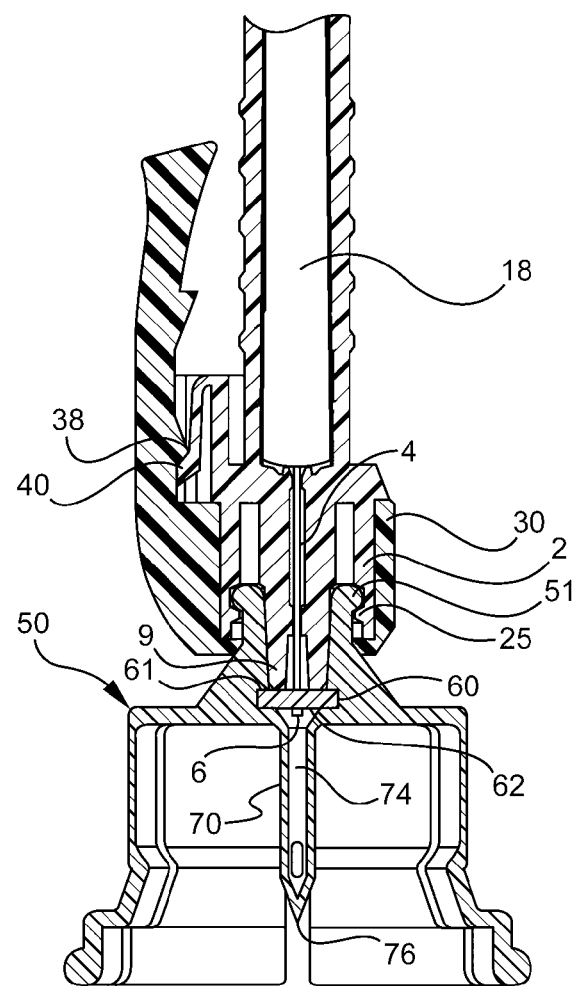
FIG. 15 shows an enlarged side cross-sectional view of the assembly of FIG. 10, with the needle inserted into the vial adapter.
Figure 16:
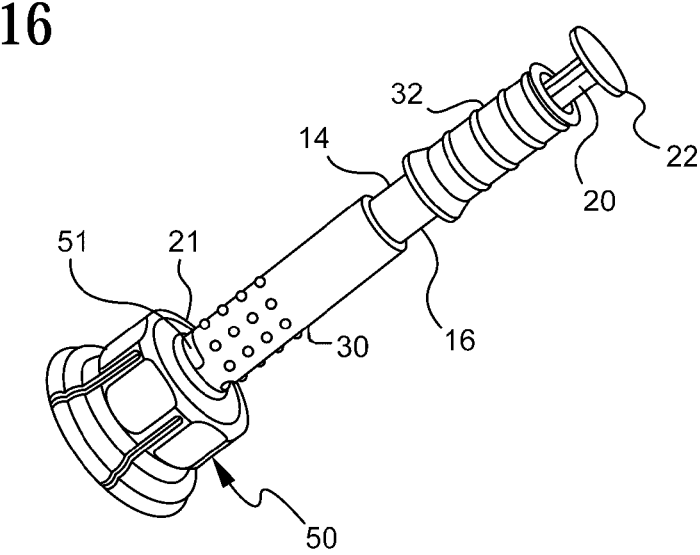
FIG. 16 shows an embodiment of an intradermal injection device having a shieldable intradermal needle assembly inserted into a vial adapter in accordance with one aspect of the invention, in perspective view.

Also shown in FIG. 10-13 is shield 30 which allows shielding the needle of the delivery device after use. Finger 32 of shield 30 having rails 41 which cooperate with grooves 42 on needle assembly 2 to allow axial movement of shield 30. Finger 32 also includes first detent 38 and second detent 36. Detents (36, 38) cooperate with lock 40 which is a cantilevered beam on needle assembly 2 to retain shield 30 in desired positions. Shield 30 is normally retained in a proximal position by first detent 38, as shown in FIG. 15, which allows needle 4 to access septum 60 of adapter 50. After use, shield 30 is moved distally and lock 40 engages second detent 36 to lock shield 30 in a distal position as shown in FIG. 13.

Figure 11:
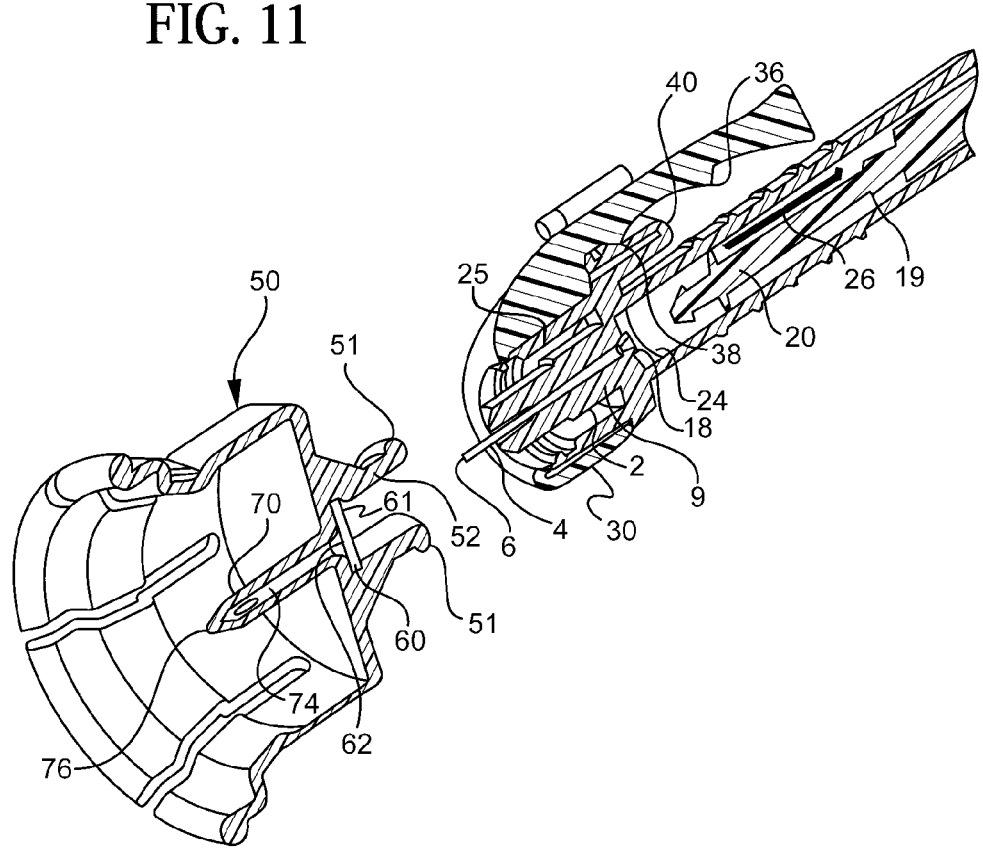
FIG. 11 shows a partial cross-sectional view of the assembly of FIG. 10.
Figure 12:
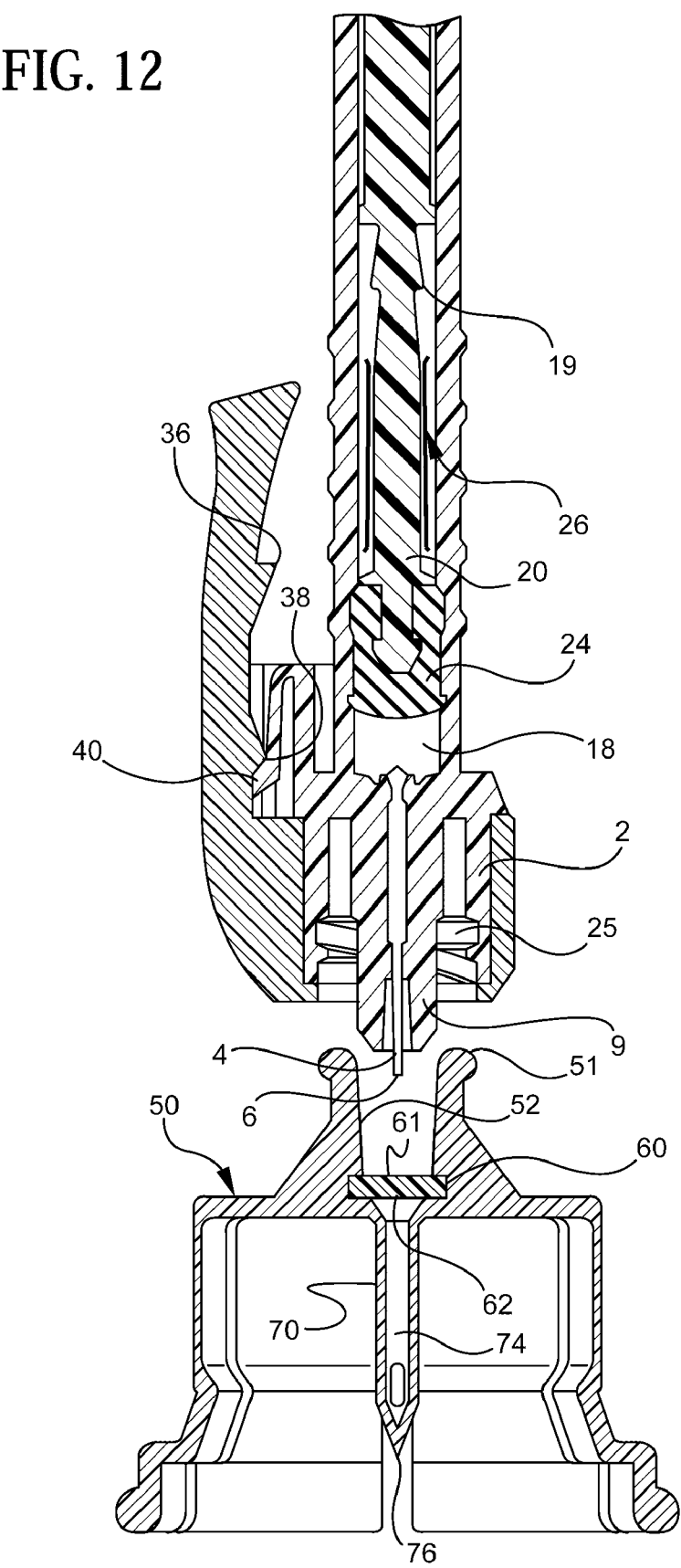
FIG. 12 shows a partial side cross-sectional view of the assembly of FIG. 10.

Also shown in FIG. 11 is plunger clip 26 which allows locking of plunger 20 within syringe body 16 after a preprescribed number of strokes as is described in co-pending US Publication 2005/0027250A1. Plunger clip 26 cooperates with plunger detents 19 and the interior wall of syringe body 16 to lock the plunger after use. The plunger clip 26, and detents 19 are selected by using skill in the art to allow the following typical stroke patterns of the plunger, wherein D=distal movement, and P=Proximal movement of the plunger: D; PD; DPD; PDPD; and PDPDPD. The plunger claip may be used in any embodiment.

Now referring to FIG. 16-20, which show an alternate embodiment having aspects of the present invention. In this particular embodiment, needle assembly 2 is assembled to syringe body 16 and preferably permanently assembled to syringe body 16, however a detachable assembly via a fitting as described previously is possible with this embodiment. Device 2 includes shield 30 which engages tang 51 on adapter 50. Shield 30 in position shown in FIG. 17 cooperating with tang 51 and tang catch 21 (disposed on shield 30 in this embodiment) allow for positive connection of the two components (Device 1 and adapter 50). In this embodiment, tang catch 21 is shown shaped in a bayonet-type connection arrangement with tang 51, however, other types of connections such as detented or threaded could be used in this application, as described previously.

In this embodiment, septum 60 is disposed in a proximal portion of protrusion 54 of adapter 50. Furthermore, septum 60 is held in place by septum retainer 64, which holds septum 60 onto adapter 50. Alternatively, septum 60 may be adhesively attached, or heat sealed onto or integrally formed into adapter 50. One advantage of having a proximally located septum is the ability to wipe the septum prior to penetration to disinfect the septum prior to use. Alternatively, the septum may be located distally on protrusion 54.

Figure 17:
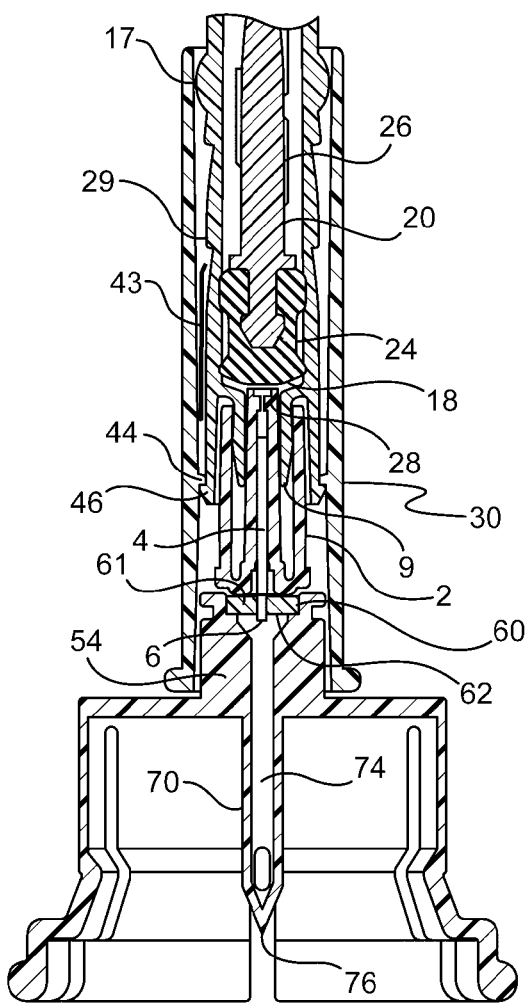
FIG. 17 shows an enlarged side cross-sectional view of the assembly of FIG. 16, with the needle inserted into the vial adapter.
Figure 18:
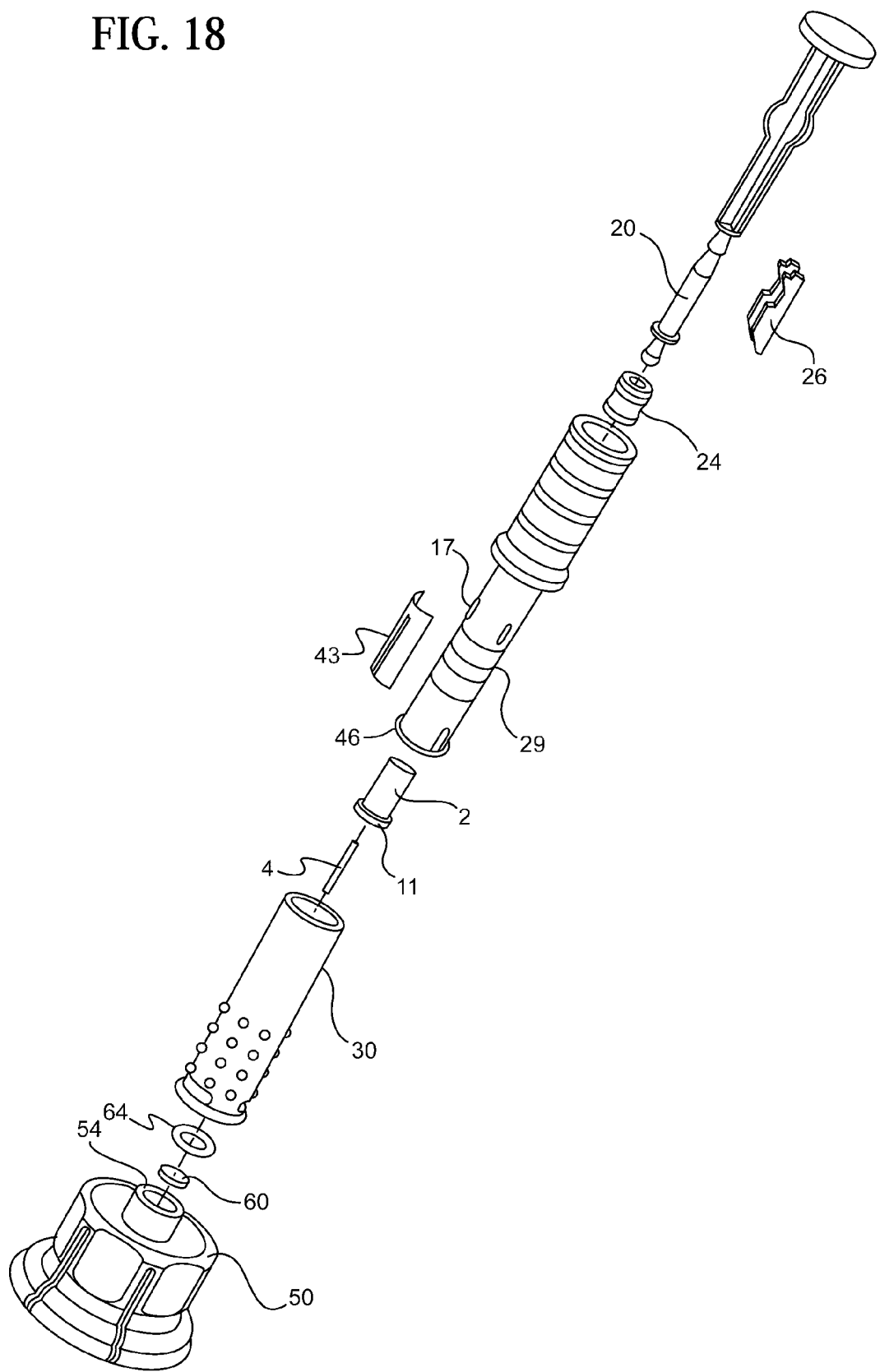
FIG. 18 shows an exploded view of the assembly of FIG. 16.
Figure 19:
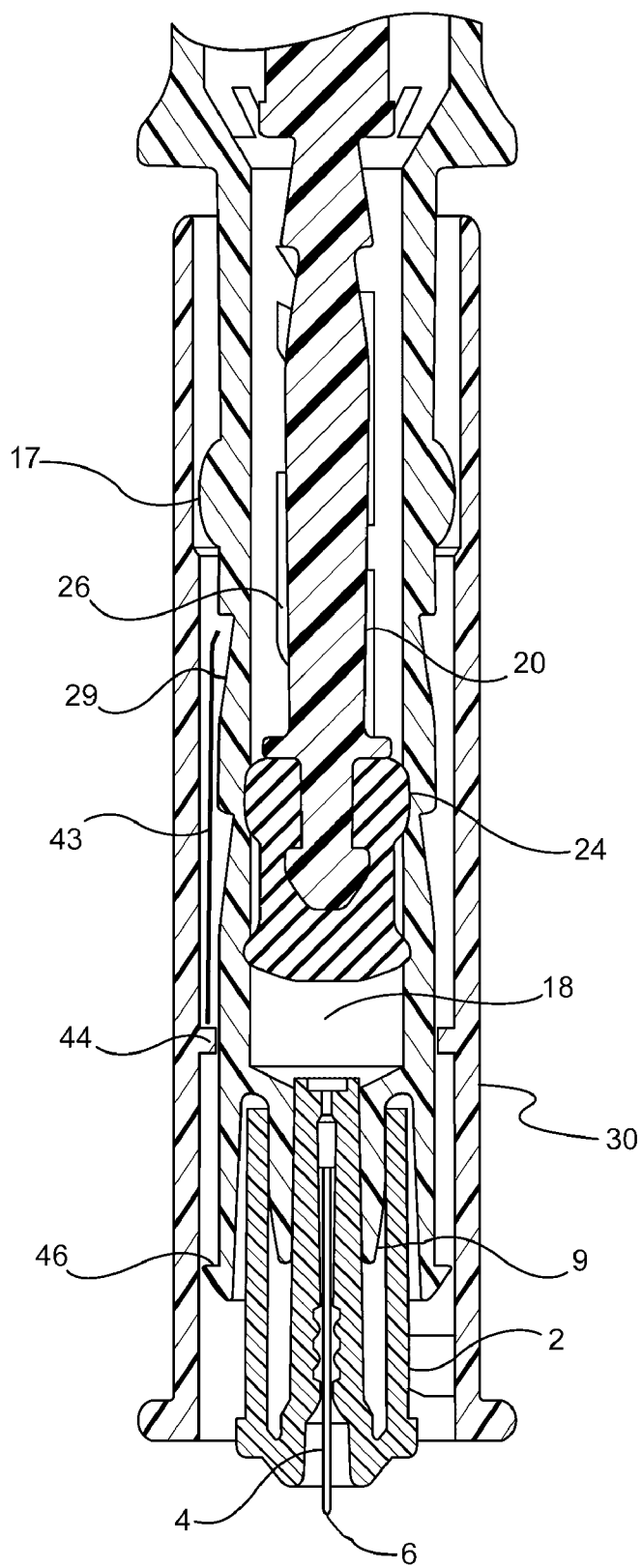
FIG. 19 shows a side cross sectional view of the intradermal device assembly of FIG. 16 with the shield in an injection position.
Figure 20:
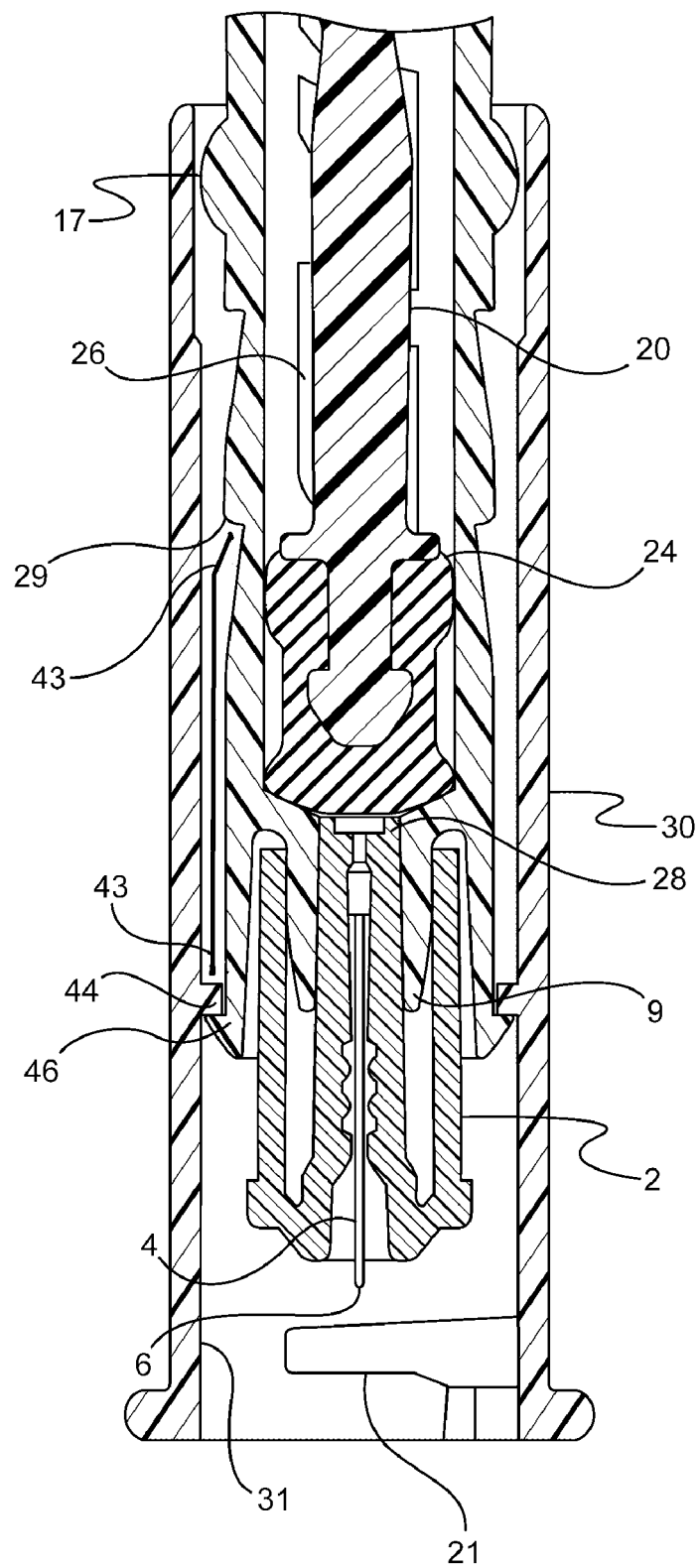
FIG. 20 shows the assembly of FIG. 19 with the shield in position after activation.

Shield 30 in this embodiment is a re-extendable shield, which locks in the extended position after use, preventing contact with the needle by use of shield clip 43. Preferably, shield 30 is first presented in the extended condition which allows easy connection of device 2 to adapter 50. Shield 30 is slidably engaged in the syringe barrel by the engagement of the shield bore 31 with barrel stop 46 and barrel guide 17 on syringe body 16. Forward stop 44 of shield 30 cooperates with barrel stop 46 to limit the distal travel of shield 30. Shield 30 is normally retained in a distal position by Forward stop 44 and barrel stop 46 along with shield clip 43, as shown in FIG. 17, which allows needle 4 to proximally located access septum 60 on protrusion 54 of adapter 50. Shield clip 43 is in a proximal position, which allows proximal movement of the shield with respect to the barrel. After filling, shield 30 is moved distally to expose needle 4 for an injection into a patient as described in detail above. The position of Shield 30 is now as is shown in FIG. 19. As shield 30 is moved distally, shield clip 43 is held in place with respect to syringe body 16, thus is in second position with respect to shield 30. After use, shield 30 is moved distally with respect to syringe body 16 and shield clip 43 engages barrel detent 29 to lock shield 30 in a distal position as shown in FIG. 20. The shield clip 43, and barrel detents 29 are selected by using skill in the art to allow the following typical stroke patterns of the shield, wherein D=distal movement, and P=Proximal movement of the plunger: D; PD; and DPD.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

What is claimed is:

1. A fluid transfer system for use in transferring a medical substance from a medication container having a septum with a thickness greater than 3 mm into a delivery device, comprising:

a reservoir within said delivery device adapted for storing a medical substance;

a needle cannula attached to said delivery device having a lumen in fluid communication to said reservoir and having a forward tip extending away from said delivery device a pre-selected usable length of less than 3 mm, such that said usable length is less than a thickness of said septum of said container;

an adapter body including:

a container receiving portion said container receiving portion having a septum access needle having a lumen, and a longitudinal projection extending from said adapter body, said projection including an adapter septum having a distal portion and a thickness that is less than the usable length of said needle cannula, wherein said distal portion is in fluid communication with said septum access needle lumen and said adapter septum is located at a proximal portion of said longitudinal projection;

wherein when said container is received in said container receiving portion and said delivery device needle is penetrated through said adapter septum, fluid communication between said substance in said container and said reservoir of said delivery device is established.

2. A system as set forth in claim 1 further comprising a shield which is slidably disposed upon said delivery device having at least a first position and a second position, said first position concealing said forward tip of said needle cannula and said second position exposing said forward tip of said needle cannula.

3. A system as set forth in claim 2 further comprising a locking clip which is slidably disposed between said shield and said delivery device having at least a first position and a second position, said first position allowing proximal movement of said shield with respect to said delivery device and said second position preventing proximal movement of said shield with respect to said delivery device.

4. A device as set forth in claim 3 wherein a first proximal movement of said shield with respect to said delivery device into said second shield position engages said locking clip and moves said locking clip into said second position of said locking clip, thereby preventing proximal movement of said shield with respect to said delivery device.

5. A method of transferring a medical substance from a medication container having a septum with a thickness greater than 3 mm into a delivery device having a reservoir in fluid communication to a needle cannula attached to said delivery device having a forward tip extending away from said delivery device a usable length less than 3 mm; comprising the steps of:
   providing an adapter including a septum access needle having a lumen, in fluid communication with a distal portion of an adapter septum having a thickness less than the usable length of said needle cannula;
   penetrating said medication container septum with said septum access needle, wherein when said container septum is penetrated with said septum access needle fluid communication between said medical substance and said lumen occurs;
   penetrating said adapter septum with said delivery device needle, wherein when said adapter septum is penetrated with said delivery device needle, fluid communication between said medical substance and said lumen occurs, whereby, fluid communication between said substance in said container and said reservoir of said delivery device is established; and,
   aspirating said medical substance into said delivery device.

6. The method of claim 5 further comprising:
   shielding said delivery device needle with a needle shield, thereby concealing said forward tip of said needle cannula, wherein said shield is slidably engaged to said delivery device.

7. The method of claim 6 further comprising:
   performing an injection with said delivery device, and locking said shield of said delivery device needle in a distal position after performing said injection step.

8. The method of claim 7 further comprising:
   providing said delivery device with said shield in an initial distal position concealing said forward tip of said needle cannula, wherein said forward tip is engageable to said adapter septum; and
   moving said shield to a proximal position exposing said usable length of said needle cannula.

9. A method of transferring a medical substance from a medication container having a septum with a pre-determined thickness into a delivery device having a reservoir in fluid communication to a needle cannula attached to said delivery device having a forward tip extending away from said delivery device a pre-selected usable length; wherein said usable length is less than said pre-determined thickness of said container septum comprising the steps of:
   providing an adapter including a septum access needle having a lumen, in fluid communication with a distal portion of an adapter septum having a thickness less than the usable length of said needle cannula;
   penetrating said medication container septum with said septum access needle, wherein when said container septum is penetrated with said septum access needle fluid communication between said medical substance and said lumen occurs;
   penetrating said adapter septum with said delivery device needle, wherein when said adapter septum is penetrated with said delivery device needle, fluid communication between said medical substance and said lumen occurs, whereby, fluid communication between said substance in said container and said reservoir of said delivery device is established;
   aspirating said medical substance into said delivery device;
   shielding said delivery device needle with a needle shield, thereby concealing said forward tip of said needle cannula, wherein said shield is slidably engaged to said delivery device;
   performing an injection with said delivery device, locking said shield of said delivery device needle in a distal position after performing said injection step;
   providing said delivery device with said shield in an initial distal position concealing said forward tip of said needle cannula, wherein said forward tip is engageable to said adapter septum; and
   moving said shield to a proximal position exposing said usable length of said needle cannula.

* * * * *